(12) United States Patent
Xue et al.

(10) Patent No.: US 11,439,565 B2
(45) Date of Patent: Sep. 13, 2022

(54) TRAINING APPARATUS

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Bangcan Xue, Beijing (CN); Yanjun Liu, Beijing (CN); Taesung Kang, Beijing (CN); Dong Zhang, Beijing (CN); Tao Jia, Beijing (CN); Liguang Deng, Beijing (CN); Jian Bai, Beijing (CN); Wenfeng Jin, Beijing (CN); Hongqiang Ji, Beijing (CN); Zhehua Long, Beijing (CN); Jia Meng, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 530 days.

(21) Appl. No.: 16/492,571

(22) PCT Filed: Feb. 18, 2019

(86) PCT No.: PCT/CN2019/075353
§ 371 (c)(1),
(2) Date: Sep. 9, 2019

(87) PCT Pub. No.: WO2019/242316
PCT Pub. Date: Dec. 26, 2019

(65) Prior Publication Data
US 2021/0322251 A1    Oct. 21, 2021

(30) Foreign Application Priority Data
Jun. 20, 2018    (CN) .......................... 201820950573.4

(51) Int. Cl.
*A61H 1/02* (2006.01)

(52) U.S. Cl.
CPC ... *A61H 1/0296* (2013.01); *A61H 2201/0103* (2013.01); *A61H 2201/0157* (2013.01);
(Continued)

(58) Field of Classification Search
CPC .......... A61H 1/0296; A61H 2201/0103; A61H 2201/0157; A61H 2201/0169;
(Continued)

(56) References Cited

U.S. PATENT DOCUMENTS 3,942,518 A    3/1976 Tenteris et al.
5,823,982 A    10/1998 Park
(Continued)

FOREIGN PATENT DOCUMENTS

CN    2127601 Y         3/1993
CN    200970291 Y *     11/2007
(Continued)

OTHER PUBLICATIONS

Translation of CN 200970291 (Year: 2007).*
(Continued)

*Primary Examiner* — Valerie L Woodward
*Assistant Examiner* — Paige Kathleen Bugg
(74) *Attorney, Agent, or Firm* — Womble Bond Dickinson (US) LLP

(57) ABSTRACT

A training apparatus is disclosed, comprising: a top structure, a bottom structure, and a traction structure disposed between the top structure and the bottom structure, and wherein the traction structure is configured to be retractable along an axial direction of the top or bottom structure to achieve relative movement between the top structure and the bottom structure.

12 Claims, 10 Drawing Sheets

(52) U.S. Cl.
CPC ............... *A61H 2201/0169* (2013.01); *A61H 2201/1238* (2013.01); *A61H 2201/165* (2013.01); *A61H 2201/1611* (2013.01); *A61H 2201/5056* (2013.01); *A61H 2201/5071* (2013.01)

(58) Field of Classification Search
CPC ..... A61H 2201/1238; A61H 2201/1609–1611; A61H 2201/165; A61H 2201/5056; A61H 2201/5071; A61H 2205/04; A61H 9/005–0092; A61F 5/055; A61F 5/56; A61F 5/04–048
USPC .......................................... 601/5, 39; 602/36
See application file for complete search history.

(56) References Cited

U.S. PATENT DOCUMENTS

| | | |
|---|---|---|
| 2006/0217647 A1 | 9/2006 | Rogachevsky |
| 2009/0204040 A1 | 8/2009 | Powell et al. |
| 2011/0172579 A1 | 7/2011 | Chiu et al. |

FOREIGN PATENT DOCUMENTS

| | | | |
|---|---|---|---|
| CN | 200970291 | Y | 11/2007 |
| CN | 104939956 | A | 9/2015 |
| CN | 105105902 | A | 12/2015 |
| CN | 105361988 | A | 3/2016 |
| CN | 206198126 | U | 5/2017 |
| CN | 207202980 | U  * | 4/2018 |
| EP | 0784968 | A1 | 7/1997 |
| WO | 2017/088335 | A1 | 6/2017 |

OTHER PUBLICATIONS

Translation of CN 207202980 (Year: 2018).*
International Search Report received for PCT Patent Application No. PCT/CN2019/075353, dated May 20, 2019, 7 pages (3 pages of English Translation and 4 pages of Original Document).
Supplementary European Search Report and Search Opinion received for EP Patent Application No. 19762280.6, dated Feb. 22, 2022, 9 pages.
Supplementary European Search Report and Search Opinion received for EP Patent Application No. 19762280.6, dated May 6, 2022, 11 pages.

* cited by examiner

TRAINING APPARATUS

RELATED APPLICATIONS

The present application is a 35 U.S.C. 371 national stage application of PCT International Application No. PCT/CN2019/075353, filed on Feb. 18, 2019, which claims the benefit of Chinese Patent Application No. 201820950573.4, filed on Jun. 20, 2018, the entire disclosures of which are incorporated herein by reference.

TECHNICAL FIELD

The present disclosure relates to the field of wearables, and more particularly to a training apparatus.

BACKGROUND

People who maintain a fixed posture for a long time will make the neck and shoulder muscles in a rigid state for a long time, which is easy to cause strain, and then cause neck diseases such as cervical disc herniation, cervical spondylosis and periarthritis of shoulder.

Since neck diseases are prone to recurrent episodes, recovery time is relatively long, professional treatment and rehabilitation training costs are high, and patients are inconvenient to move, at present, the neck training is mainly performed by specialized medical instruments that are towed by multiple degrees of freedom. The characteristics of these instruments comprise at least a complicated structure, a large volume, an expensive price, and are not easy to operate.

SUMMARY

It is an object of the present disclosure to provide a training apparatus for cervical vertebra rehabilitation.

According to one aspect of the present disclosure, there is provided a training apparatus comprising: a top structure, a bottom structure, and a traction structure disposed between the top structure and the bottom structure, and wherein the traction structure is configured to be retractable along an axial direction of the top or bottom structure to achieve relative movement between the top structure and the bottom structure.

In some embodiments of the training apparatus according to the present disclosure, the traction structure comprises a plurality of traction sub-structures, each of the plurality of traction sub-structures being configured to be independently retractable along the axial direction.

In some embodiments of the training apparatus according to the present disclosure, the training apparatus further comprises: a top bracket disposed between the top structure and the traction structure, and a bottom bracket disposed between the bottom structure and the traction structure.

In some embodiments of the training apparatus according to the present disclosure, each of the top bracket and the bottom bracket comprises annular structure, and the plurality of traction sub-structures are disposed on the bottom bracket to be connected to the top bracket, and the plurality of traction sub-structures are sequentially spaced along the annular structure.

In some embodiments of the training apparatus according to the present disclosure, each of the plurality of traction sub-structures comprises an inflatable stacked structure, each stack of the stacked structure is stacked along a direction from the bottom structure to the top structure, and the stacked structure is configured to be a flat shape in an uninflated state and a stretched shape in an inflated state, and achieve the relative movement between the top structure and the bottom structure by inflation and deflation.

In some embodiments of the training apparatus according to the present disclosure, the number of the plurality of traction sub-structures is 7-9.

In some embodiments of the training apparatus according to the present disclosure, the stacked structure comprises a plurality of rubber tubes stacked and in communication with each other.

In some embodiments of the training apparatus according to the present disclosure, in the stacked structure, a top rubber tube and a bottom rubber tube respectively have one opening, and the rubber tubes between the top rubber tube and the bottom rubber tube each have both an upper opening and a lower opening, and adjacent rubber tubes communicate through adjacent openings.

In some embodiments of the training apparatus according to the present disclosure, a side of each of the top rubber tube and the bottom rubber tube closer to an adjacent rubber tube is provided with two stuck slots located on both sides of the opening and extending along a direction of the opening, a side of the top bracket closer to the rubber tube is provided with a first stuck slot that is matched with the stuck slot of the top rubber tube; and a side of the bottom bracket closer to the rubber tube is provided with a second stuck slot that is matched with the stuck slot of the bottom rubber tube.

In some embodiments of the training apparatus according to the present disclosure, a side of the top bracket away from the rubber tube is provided with a first groove configured to receive the top structure; and a side of the bottom bracket away from the rubber tube is provided with a second groove configured to receive the bottom structure.

In some embodiments of the training apparatus according to the present disclosure, the top structure and the bottom structure comprise annular airbags.

In some embodiments of the training apparatus according to the present disclosure, the annular airbag of the top structure comprises: a notch, and two protrusions, the two protrusions being inflatable structures integrally designed with the annular airbag.

In some embodiments of the training apparatus according to the present disclosure, the training apparatus further comprises a drive device configured to control extension and retraction of the plurality of traction sub-structures, and wherein the drive device comprises: an inflation mechanism configured to inflate each of the stacked structures; a plurality of pairs of switching valves configured to respectively control inflation and deflation of each of the stacked structures, each pair of switching valves comprising an inflation valve and a deflation valve; and a control mechanism configured to control the inflation mechanism and the plurality of pairs of switching valves.

In some embodiments of the training apparatus according to the present disclosure, the inflation valve and the deflation valve comprise solenoid valves or electric valves, and the inflation valve and the deflation valve are independently controllable.

In some embodiments of the training apparatus according to the present disclosure, the inflation mechanism comprises: one or more air pumps configured to generate a source gas; an air sack configured to be connected to the air pumps to store the source gas; and an intake valve connected to an outlet end of the air sack, wherein the control mechanism is configured to control the turning on and turning off of the intake valve.

In some embodiments of the training apparatus according to the present disclosure, the inflation mechanism further comprises: a first air pressure sensor connected between the air pumps and the air sack, the first air pressure sensor being configured to sense an internal pressure of the air sack, wherein the control mechanism is configured to: compare the pressure sensed by the first air pressure sensor with a preset upper threshold and a preset lower threshold, and turn off the air pumps in response to the sensed pressure being greater than the upper threshold, and turn on the air pump in response to the sensed pressure being less than the lower threshold.

In some embodiments of the training apparatus according to the present disclosure, each of the plurality of pairs of switching valves further comprises: a second air pressure sensor disposed at an outlet end of the inflation valve, the second air pressure sensor being configured to sense an air pressure in the stacked structure, wherein the control mechanism is configured to turn on and turn off the inflation valve and/or the deflation valve according to the air pressure sensed by the second air pressure sensor.

In some embodiments of the training apparatus according to the present disclosure, the inflation mechanism further comprises: an F.R.L connected between the intake valve and the pair of switching valves.

In some embodiments of the training apparatus according to the present disclosure, the drive device further comprises a memory configured to store operational steps of a predetermined traction movement, and wherein the control mechanism is configured to control the plurality of pairs of switching valves according to the operational steps of the predetermined traction movement stored in the memory.

In some embodiments of the training apparatus according to the present disclosure, each deflation valve of the plurality of pairs of switching valves comprises a muffler disposed at an outlet end of the deflation valve.

In some embodiments of the training apparatus according to the present disclosure, the predetermined traction movement comprises forward flexion and backwards extension movements in a sagittal plane, left and right flexion movements in a coronal plane, a rotational movement in a horizontal plane, and a tensile traction movement in a vertical direction.

BRIEF DESCRIPTION OF THE DRAWINGS

The various aspects, features, and advantages of the present disclosure will be readily understood from the following detailed description and drawings, in which.

It should be noted that, the above drawings are merely schematic and illustrative, and are not necessarily drawn to scale.

DETAILED DESCRIPTION OF EMBODIMENTS

Figure 1A:
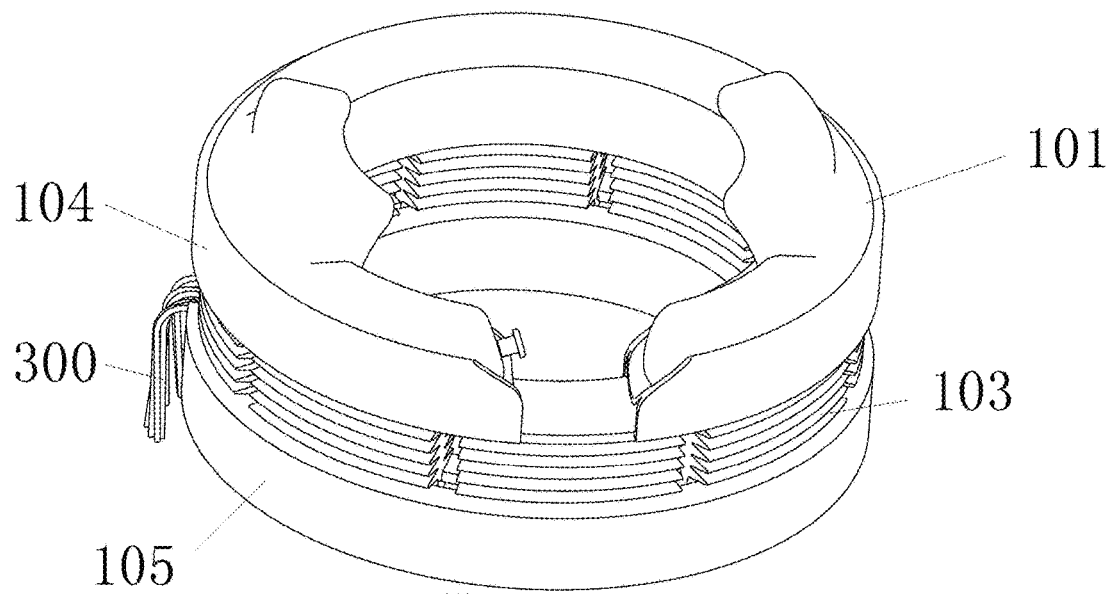
FIG. 1a schematically illustrates a perspective front view of a training apparatus in accordance with some embodiments of the present disclosure.
Figure 1B:
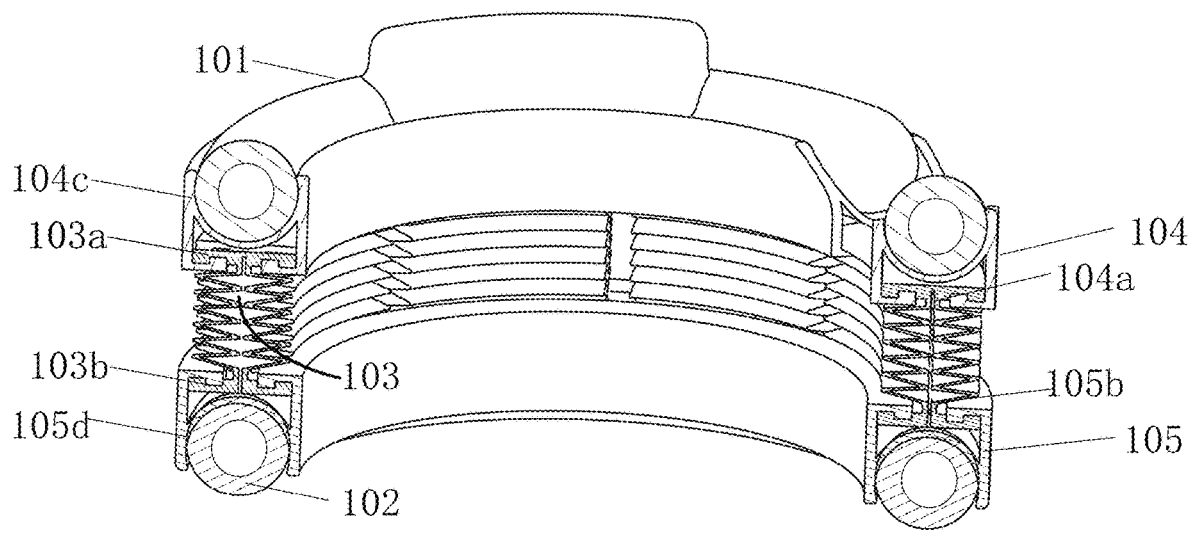
FIG. 1b schematically illustrates a cross-sectional view of a training apparatus in accordance with some embodiments of the present disclosure.

The disclosure will be described more fully with reference to the accompanying drawings below. Some embodiments of the present disclosure are shown in the drawings FIGS. 1a-1b schematically illustrate front and cross-sectional views of a training apparatus in accordance with some embodiments of the present disclosure, respectively. As shown in FIGS. 1a-1b, a training apparatus according to some embodiments of the present disclosure may comprise a top structure 101, a bottom structure 102, and a traction structure 103 disposed between the top structure 101 and the bottom structure 102, wherein the traction structure 103 is configured to be retractable along an axial direction of the top structure 101 or the bottom structure 102 to achieve relative movement between the top structure 101 and the bottom structure 102. In the training apparatus according to some embodiments of the present disclosure, the traction structure 103 is axially extended and retracted, thereby achieving the purpose of assisting the movement of body parts required activities, such as neck, the joint portion, and the like. Illustratively, the training apparatus according to some embodiments of the present disclosure may assist a normal person in performing neck activities, or assist a patient with cervical spondylosis to perform neck activities to relieve or treat the pain. Moreover, the above-mentioned training apparatus is simple in structure, portable and light, and low in cost, and thus is suitable for home exercise or rehabilitation.

In some embodiments of the training apparatus according to the present disclosure, the top structure and the bottom structure may be annular structures, and the traction structure may also be an annular structure matching the top structure and the bottom structure. The part of the trained object can be projected into the annular structure to obtain auxiliary movement in a movement state in which the traction structure is axially extended and retracted.

A training apparatus according to some embodiments of the present disclosure may be a training apparatus for a certain active position of a trained object, e.g. a training apparatus for the joints of a human or an animal, such as neck, arm, and leg, or the like. In the following description of the present disclosure, a neck training apparatus is mainly taken as an example for explanation.

In some embodiments of the training apparatus according to the present disclosure, the traction structure comprises a plurality of traction sub-structures, each of the plurality of traction sub-structures is configured to be independently retractable along the axial direction. The traction sub-structures can be independently controlled with each other, which can adapt to the autonomic activities of the trained object. For example, when the trained object moves to a certain direction, the plurality of traction sub-structures can be respectively controlled to adapt to the moving direction of the trained object, thus improving the positive effects of training and reducing the negative effects of training. In some implementations, the training apparatus according to the present disclosure further comprises a top bracket disposed between the top structure and the traction structure, and a bottom bracket disposed between the bottom structure and the traction structure.

As shown in FIGS. 1a and 1b, in some embodiments, the training apparatus can further comprise a top bracket 104 disposed between the top structure 101 and the traction structure 103 for receiving and fixing the top structure 101, and a bottom bracket 105 disposed between the bottom structure 102 and the traction structure 103 for fixing the bottom structure 102. The traction structure 103 can be detachably connected between the top bracket 104 and the bottom bracket 105.

FIGS. 2a-2e schematically illustrate perspective views of various components of a training apparatus in accordance with some embodiments of the present disclosure, respectively.

Figure 2A:
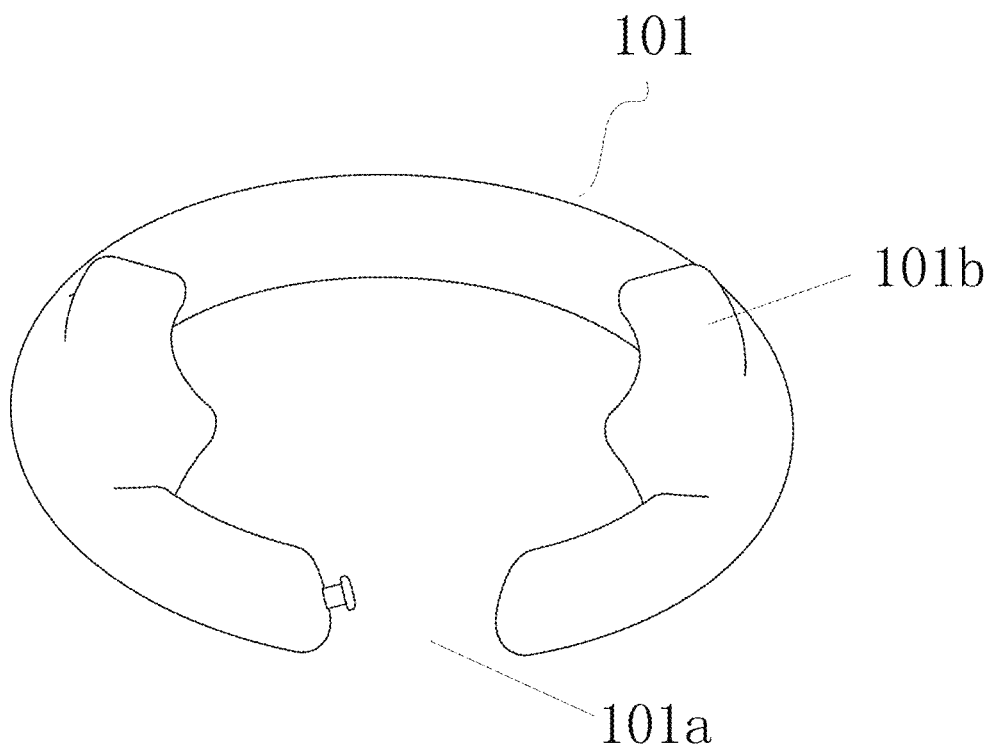
FIGS. 2a, 2b, 2c, 2d, and 2e schematically illustrate perspective views of a top structure, a top bracket, a bottom bracket, a bottom structure, and a traction structure of a training apparatus in accordance with some embodiments of the present disclosure, respectively.
Figure 2B:
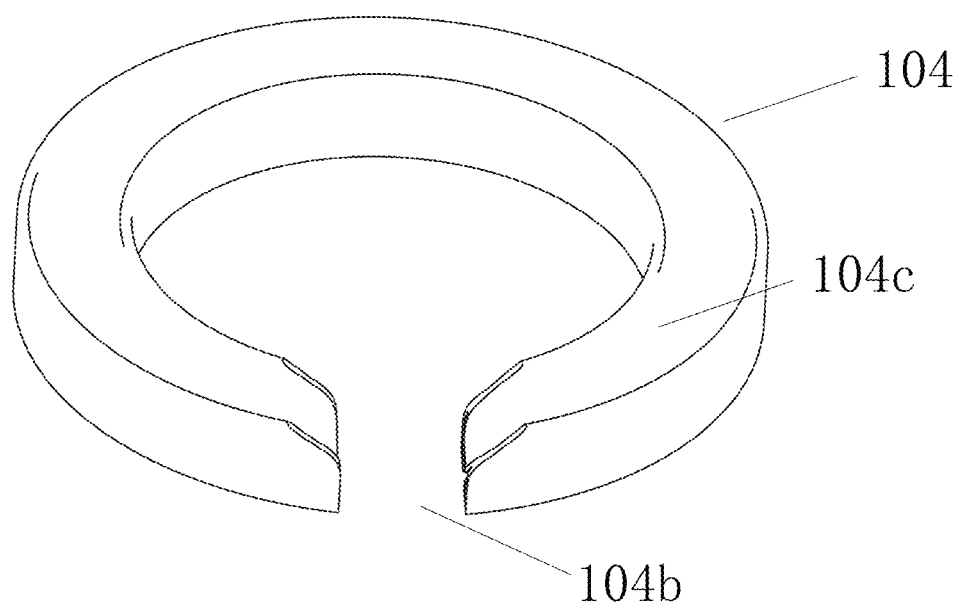
Figure 2C:
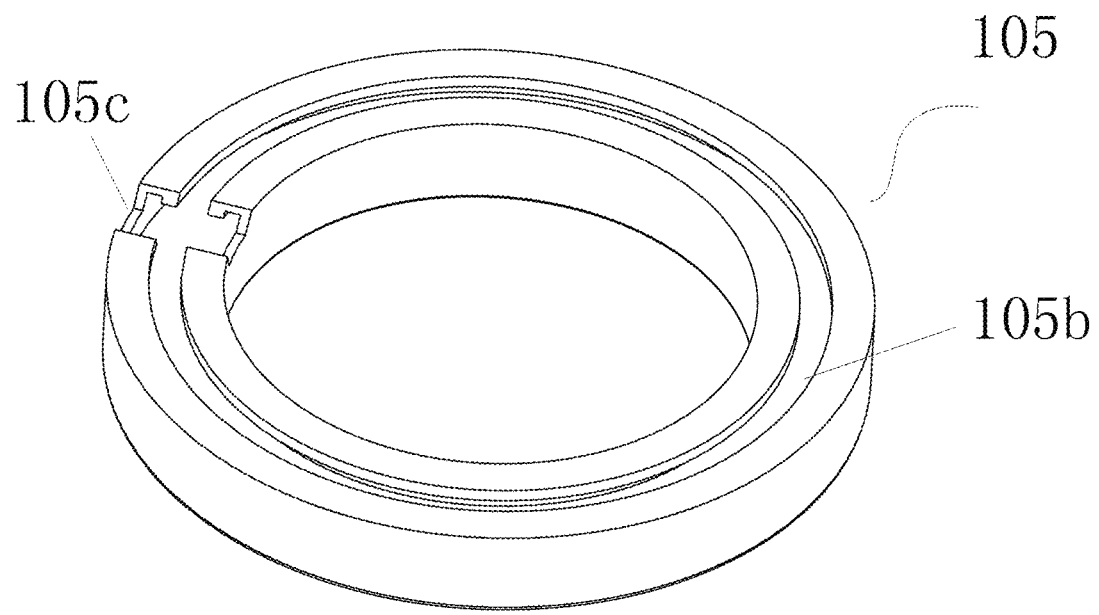
Figure 2D:
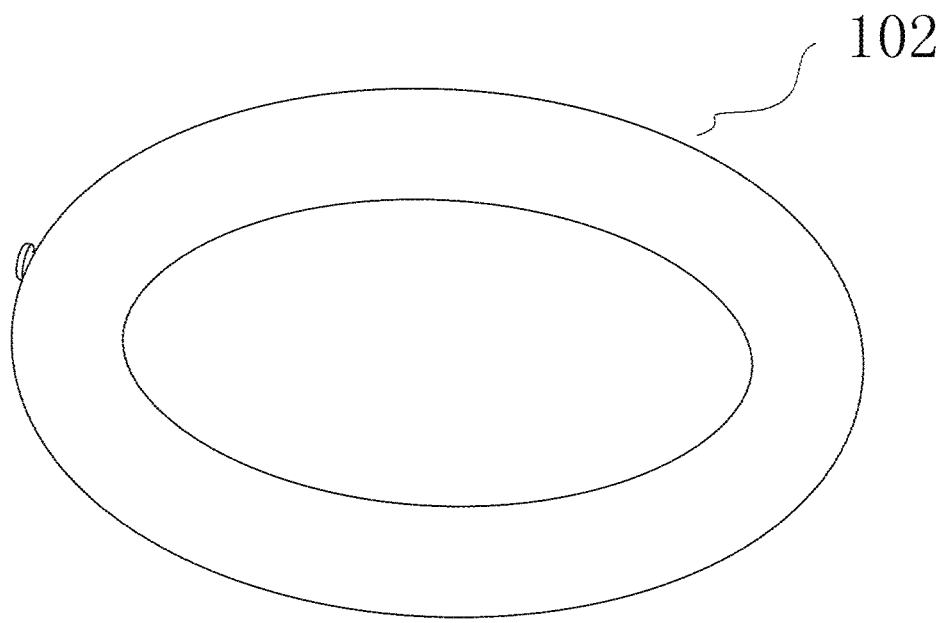

FIGS. 2a and 2d illustrate a top structure 101 and a bottom structure 102 of a training apparatus in accordance with some embodiments of the present disclosure, respectively. In some embodiments in accordance with the present disclosure, the top structure 101 and the bottom structure 102 can be flexible structures, such as the annular airbags illustrated in FIGS. 2a and 2d, namely the top and bottom airbags. Since the top structure 101 and the bottom structure 102 need to be in direct contact with the trained object (e.g., the human body), the structure such as an airbag can improve wearing comfort. The top and bottom airbags may take the form of inflatable airbags. As shown in FIGS. 2a and 2d, the top and bottom airbags may be in the shape of a ring similar to a tire after inflation.

Since the airbag is small in volume before being inflated, the top airbag and the bottom airbag can be kept in an uninflated state before the training apparatus is worn, so as to be easy to wear, store and carry. And the airbag has a certain elasticity and flexibility after being inflated, thereby wear comfort is achieved when the training apparatus is operated. In addition, in the inflated state, because of the better flexibility and toughness of the airbag, the top airbag can fully contact the wearer's head to support the weight of the wearer's head. At the same time, it is also the direct force point when towing the neck. In addition, the inflation and deflation of the top and bottom airbags may be performed by means of an external electric or manual air pump, or may be controlled by a dedicated control device.

In some embodiments of the present disclosure, as shown in FIG. 2a, the top structure 101 can comprise a notch 101a configured to correspond to a position of a wearer's lower jaw (commonly known as a chin) when worn by the wearer to fit the lower jaw, thereby improving wear comfort. Furthermore, as shown in FIG. 2a, the top structure 101 may further comprise at least one protrusion 101b configured to support the wearer's neck and/or head (two protrusions 101b corresponding to for example the human shoulder positions are exemplarily shown in FIG. 2a). The at least one protrusion 101b as shown is mainly used to contact the neck and/or the head of the human body when worn to support the neck or the head, and thus its structure should be adapted to the contours of the corresponding portions of the human neck and/or head, to further improve wear comfort. Optionally, when the top structure 101 is an annular airbag, the at least one protrusion 101b is an inflatable structure integrally designed with the annular airbag.

FIG. 2b illustrates a top bracket 104 of a training apparatus in accordance with some embodiments of the present disclosure. As shown in FIGS. 2b and 1b, the top bracket 104 can comprise a first groove 104c for receiving the top structure 101. In some embodiments, the top bracket 104 can comprise a notch 104b. The notch 104b correspondingly matches with the notch 101a of the top airbag 101 as shown in FIG. 2a, which is carried by the notch 104b. Optionally, as shown in FIG. 1b, the lower portion of the top bracket 104 may be provided with a first stuck slot 104a (not shown in FIG. 2b) for connection to the traction structure 103.

FIG. 2c illustrates a bottom bracket 105 of a training apparatus in accordance with some embodiments of the present disclosure. As shown in FIGS. 2c and 1b, the bottom bracket 105 can be annular and its upper portion is provided with a second stuck slot 105b for connection to the traction structure 103. As shown in FIG. 2c, the bottom bracket 105 may further be provided with a cove 105c for placing a connecting structure connected to the external device, e.g., a connection line for connecting an air pump that inflates the airbag when the top structure 101 or the bottom structure 102 is an airbag. Further, as shown in FIG. 1b, the lower portion of the bottom bracket 105 may be provided with a second groove 105d (not shown in FIG. 2c) similar to the first groove 104c of the top bracket 104 for receiving the bottom structure 102.

In some embodiments of the training apparatus according to the present disclosure, as shown in FIGS. 1a and 1b, the first groove 104c of the top bracket 104 and the second groove 105d of the bottom bracket 105 may be annular grooves, and the opening directions of the two grooves are opposite, that is, the first groove 104c faces upward and the second groove 105d faces downward. The top structure 101 and the bottom structure 102 can be connected to the top bracket 104 and the bottom bracket 105, respectively, in a detachable manner, such as a snap fit. For example, when the top structure 101 and the bottom structure 102 are annular inflatable airbags, as shown in FIG. 1b, in the inflated state, the top structure 101 and the bottom structure 102 are respectively snap fitted into the first groove 104c of the top bracket 104 and the second groove 105d of the bottom bracket 105.

In some embodiments, as shown in FIG. 2b, the inner diameter of the circular section of the first groove 104c of the upper portion of the top bracket 104 is the same as the outer diameter of the circular section of the top structure 101, thereby achieving a close match between the two. Moreover, the height value of the first groove 104c of the upper portion of the top bracket 104 exceeds the inner diameter value of its circular section, and the top bracket 104 is bent inward at an angle on both sides of the tail portion of the first groove 104c, so that when in an inflated state the top structure 101 can be more securely snap fitted into the first groove 104c of the top bracket 104, the top structure 101 and the top bracket 104 can be integrated into one whole without being easily separated, and the top bracket 104 functions to fix the top structure 101.

In some embodiments, as shown in FIG. 2c, the inner diameter of the circular section of the second groove 105d of the lower portion of the bottom bracket 105 is the same as the outer diameter of the circular section of the bottom structure 102, thereby achieving a close match between the two. Moreover, the height value of the second groove 105d of the lower portion of the bottom bracket 105 exceeds the inner diameter value of its circular section, and the bottom bracket 105 is bent inward at an angle on both sides of the tail portion of the second groove 105d, so that when in an inflated state the bottom structure 102 can be more securely snap fitted into the second groove 105d of the bottom bracket 105, avoiding to be separated from it, and the bottom bracket 105 functions to fix the bottom structure 102.

Figure 3A:
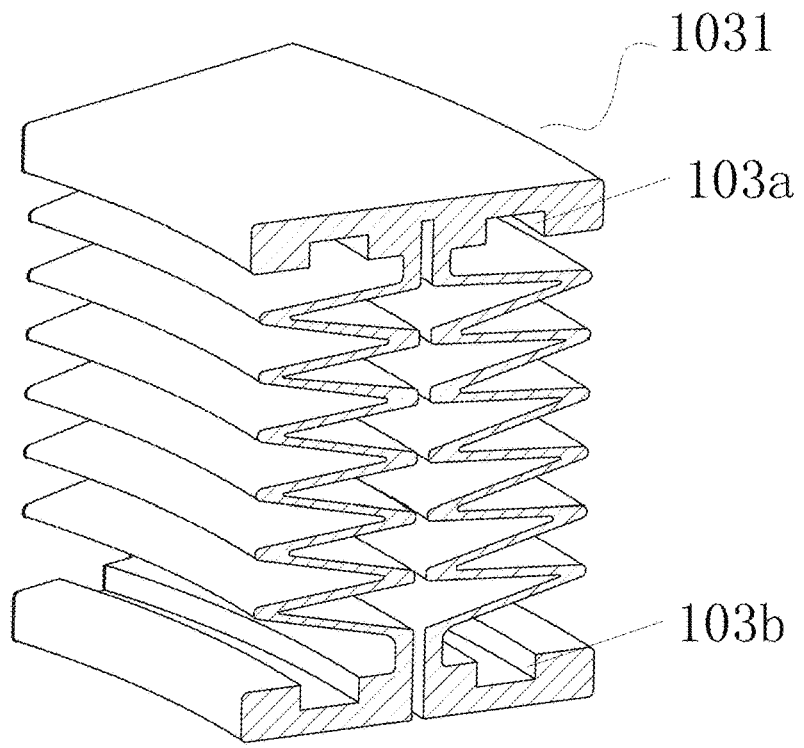
FIGS. 3a-3b schematically illustrate cross-sectional views of a traction sub-structure of a training apparatus in an uninflated state and an inflated state in accordance with some embodiments of the present disclosure, respectively.

In some embodiments, as shown in FIG. 3a, the traction structure 103 can be a retractable structure, such as an inflatable stacked structure having an upper trench 103a and a lower trench 103b. The upper trench 103a and the lower trench 103b are respectively configured to match the first stuck slot 104a of the lower portion of the top bracket 104 and the second stuck slot 105b of the upper portion of the bottom bracket 105. Therefore, when connecting, the upper trench 103a of the traction structure 103 is directly snap fitted into the first stuck slot 104a of the top bracket 104, and the lower trench 103b of the traction structure 103 is directly snap fitted into the second stuck slot 105b of the bottom bracket 105.

Figure 2E:
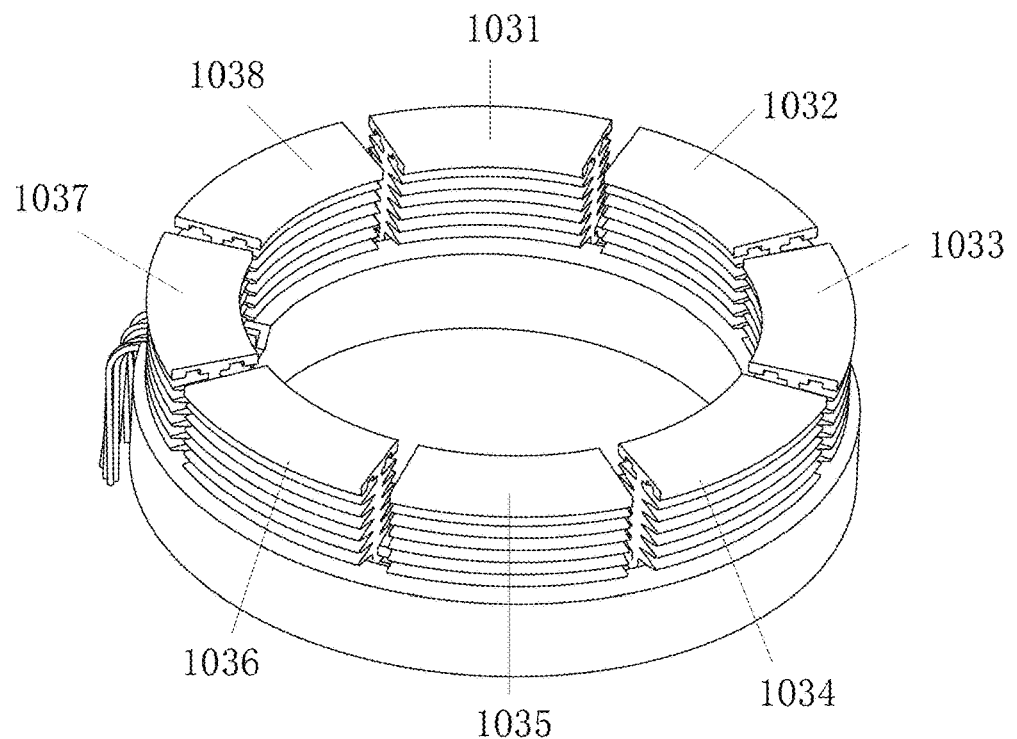

FIG. 2e shows a plurality of traction sub-structures 1031 to 1038 of the traction structure 103 of the training apparatus according to the present disclosure. In some embodiments, as shown in FIG. 2e, the traction structure 103 of the training apparatus can comprise a plurality of traction sub-structures 1031 to 1038, wherein each of the traction sub-structures 1031 to 1038 can be configured to be independently retractable along the axial direction of the top structure 101 or the bottom structure 102. As shown in FIGS. 1a and 2e, the top bracket 104 and the bottom bracket 105 are annular structures, and the plurality of traction sub-structures 1031 to 1038 are disposed on the bottom bracket 105 to be connected to the top bracket 104. The plurality of traction sub-structures 1031 to 1038 are sequentially spaced along the annular structure.

According to the principle of human physiology, the neck movement of the human body is mainly caused by the retraction and stretching of the muscle tissue distributed around the neck to complete the multi-degree-of-freedom movement of the human neck. According to the freedom of movement of the human neck and the composition of the muscle tissue that drives the neck movement, the complex and minute muscle tissues can be neglected, and the muscle tissues that play the movement and traction function can be simplified into several major muscle tissues. For example, they can be simplified into the following eight muscle tissues around the neck: the erector spinae at the direct rear side, the left trapezius at the left rear side, the left sternocleidomastoid at the left side, the left platysma at the left front side, the sternohyoid muscle at the direct front side, the right platysma at the right front side, the right sternocleidomastoid at the right side, and the right trapezius at the right rear side. Thus, according to the bionics principle, the plurality of traction sub-structures 1031-1038 shown in FIG. 3 that can be independently retractable along the axial direction can be configured to correspond to the positions of different muscle tissues around the neck when worn by the wearer. By simulating respective major muscle tissue around the human neck that plays the movement and traction function, the plurality of traction sub-structures 1031-1038 are retracted and stretched to drive the top structure 101 to complete multi-directional, multi-angle, and multi-dimensional traction of the human neck.

In the concepts of mathematics and physics, "axial direction" is usually for a cylindrical object, that is, the direction of the central axis of rotation of the cylinder, i.e., the direction common to the central axis. Therefore, "axial movement" is the movement along the axial direction, that is, the movement along the direction of the central axis of rotation. In the present disclosure, as shown in FIG. 2e, in order to match the contours of the neck and the head of the human body, the top structure, the bottom structure, the traction structure, and the like are generally annular, and thus belong to cylindrical object that is symmetric about the center of rotation. Accordingly, "axial extension and retraction or axial movement" of the traction structure or traction sub-structure as referred to herein refers to movement along a central axis of rotation of the top structure, the bottom structure, or the traction structure, i.e., movement in a substantially vertical direction, thereby driving the top structure to tow the neck. Generally, the axial retractable movement of each of the plurality of traction sub-structures 1031-1038 can be performed separately or independently to drive the movement of the top structure, to achieve flexible traction of the neck. Of course, some or all of the plurality of traction sub-structures 1031-1038 can also be retractable along the axial direction in a coordinated manner to achieve diverse neck traction.

For example, the traction sub-structures 1031-1038 as shown in FIG. 2e may be configured to correspond to the positions of the above-described erector spinae at the direct rear side, the left trapezius at the left rear side, the left sternocleidomastoid at the left side, the left platysma at the left front side, the sternohyoid muscle at the direct front side, the right platysma at the right front side, the right sternocleidomastoid at the right side, and the right trapezius at the right rear side around the neck, respectively. Therefore, the retraction and/or extension movement of the respective muscle tissue can be simulated, and the retractable movement of the respective traction sub-structures 1031-1038 can cooperate to each other, for example, to achieve traction movement of at least 4 degrees of freedom, such as but not limited to, forward flexion/backwards extension movement in a sagittal plane, left/right flexion movement in a coronal plane, a rotational movement in a horizontal plane, and a tensile traction movement in a vertical direction.

The principle of using a plurality of retractable traction sub-structures 1031-1038 to achieve multi-degree-of-freedom (here, 4 degrees of freedom is taken as an example) traction movement is described below with reference to FIG. 2e.

1. The forward flexion/backwards extension movement in a sagittal plane: the first traction sub-structure 1031 corresponding to the erector spinae performs the extension movement in the vertical axial direction, while the fifth traction sub-structure 1035 corresponding to the sternohyoid muscle performs the retraction movement in the vertical axial direction, thereby pushing the top structure 101 to perform the forward flexion movement of a sagittal plane, and driving the wearer's neck to complete the forward flexion movement of a sagittal plane. Conversely, the fifth traction sub-structure 1035 corresponding to the sternohyoid muscle performs the extension movement in the vertical axial direction, while the first traction sub-structure 1031 corresponding to the erector spinae performs the retraction movement in the vertical axial direction, thereby pushing the top structure 101 to perform the backwards extension movement of a sagittal plane, and driving the wearer's neck to complete the backwards extension movement of a sagittal plane.

2. The left/right flexion movement in a coronal plane: the third traction sub-structure 1033 corresponding to the left sternocleidomastoid performs the extension movement in the vertical axial direction, while the seventh traction sub-structure 1037 corresponding to the right sternocleidomastoid performs retraction movement in the vertical axial direction, thereby driving the wearer's neck to complete the right flexion movement of the coronal plane. Conversely, the seventh traction sub-structure 1037 performs extension movement in the vertical axial direction, while the third traction sub-structure 1033 performs the retraction movement in the vertical axial direction, thereby driving the wearer's neck to complete the left flexion movement of the coronal plane.

Similarly, the fourth traction sub-structure 1034 corresponding to the left platysma performs extension movement in the vertical axial direction, while the eighth traction sub-structure 1038 corresponding to the right trapezius performs retraction movement in the vertical axial direction, to achieve the bending movement of the human neck toward the right rear. On the contrary, the eighth traction sub-structure 1038 performs extension movement in the vertical axial direction, while the fourth traction sub-structure 1034 performs retraction movement in the vertical axial direction, to achieve the bending movement of the human neck toward the left front. Furthermore, the sixth traction sub-structure 1036 corresponding to the right platysma performs extension movement in the vertical axial direction, while the second traction sub-structure 1032 corresponding to the left trapezius performs retraction movement in the vertical axial direction, to achieve the bending movement of the human neck toward the left rear. Conversely, the second traction sub-structure 1032 performs extension movement in the vertical axial direction, while the sixth traction sub-structure 1036 performs retraction movement in the vertical axial direction, to achieve the bending movement of the human neck toward the right front.

3. The rotational movement in a horizontal plane: the first, second, third, fourth, fifth, sixth, seventh, and eighth traction sub-structures 1031-1038 corresponding to the erector spinae, left trapezius, left sternocleidomastoid, left platysma, sternohyoid muscle, right platysma, right sternocleidomastoid, right trapezius sequentially perform extension movement in the vertical axial direction in a clockwise order, while the traction sub-structure opposite to the traction sub-structure which is performing the extension movement performs retraction movement in the vertical axial direction. That is, the first traction sub-structure 1031 performs extension movement, while the fifth traction sub-structure 1035 opposite thereto performs retraction movement in the vertical axial direction; the second traction sub-structure 1032 performs extension movement, while the sixth traction sub-structure 1036 opposite thereto performs retraction movement in the vertical axial direction; the third traction sub-structure 1033 performs extension movement, while the seventh traction sub-structure 1037 opposite thereto performs retraction movement in the vertical axial direction; the fourth traction sub-structure 1034 performs extension movement, while the eighth traction sub-structure 1038 opposite thereto performs retraction movement in the vertical axial direction; the fifth traction sub-structure 1035 performs extension movement, while the first traction sub-structure 1031 opposite thereto performs retraction movement in the vertical axial direction; the sixth traction sub-structure 1036 performs extension movement, while the second traction sub-structure 1032 opposite thereto performs retraction movement in the vertical axial direction; the seventh traction sub-structure 1037 performs extension movement, while the third traction sub-structure 1033 opposite thereto performs retraction movement in the vertical axial direction; the eighth traction sub-structure 1038 performs extension movement, while the fourth traction sub-structure 1034 opposite thereto performs retraction movement in the vertical axial direction, so that the wearer's neck can be driven to complete the clockwise rotational movement of the horizontal plane. Conversely, if the eight traction sub-structures 1031-1038 sequentially perform extension movement in the vertical axial direction in a counterclockwise order, while the traction sub-structure opposite to the traction sub-structure which is performing extension movement performs retraction movement, the wearer's neck can be driven to complete the counterclockwise rotational movement of the horizontal plane.

4. The tensile traction movement in a vertical direction (i.e., the axial direction): the eight traction sub-structures 1031-1038 simultaneously perform extension movement in the vertical axial direction, and the wearer's neck can be driven to complete the tensile traction movement in the vertical direction.

According to the above description, the training apparatus according to the present disclosure simulates the extension and retraction of the corresponding muscle tissues by using a plurality of retractable traction sub-structures 1031-1038 respectively corresponding to the positions of the plurality of main muscle tissues around the neck that play traction functions, thereby achieving multi-degree-of-freedom (i.e. multi-angle, multi-directional, multi-dimensional) traction and stretching movement to the neck, to achieve the purpose of neck and cervical rehabilitation training. The above 4-degree-of-freedom traction movement is merely an example or as a preset traction movement mode to achieve a basic traction and stretching to the neck. On this basis, the user can design a plurality of personalized traction movement modes according to his or her own needs and actual conditions.

Optionally, each of the traction sub-structures can be controlled cooperatively or independently. In some embodiments, the control of each of the traction sub-structures can be performed simultaneously or with a time difference between each other. This allows the traction sub-structures to cooperate with each other to complete the drive of the top bracket and the top structure, thereby completing the rehabilitation training tasks for the user's (i.e., the wearer's) neck.

The training apparatus according to the present disclosure can achieve traction on the wearer's neck by simulating the neck muscle tissue by the retractable traction structure according to the bionic design, thereby reducing the pressure on the cervical vertebrae of the head, relieving the muscle spasm of the neck, increasing the distance between the vertebral bodies, relieving the neck nerve roots, muscles, cervical vertebrae from the pressure or stimulation, and achieving the purpose of exercising the neck muscles and treating cervical spondylosis. Further, the cervical vertebra rehabilitation training apparatus according to the present disclosure makes the top and bottom structures directly contact the neck and/or the head and their surrounding skins, achieving comfortable wearing and traction. Therefore, the training apparatus of the present disclosure has the advantages of simple structure, portability, flexibility, comfortable wearing, low cost, and the like, and can be widely applied to the field of home rehabilitation medical services.

Figure 3B:
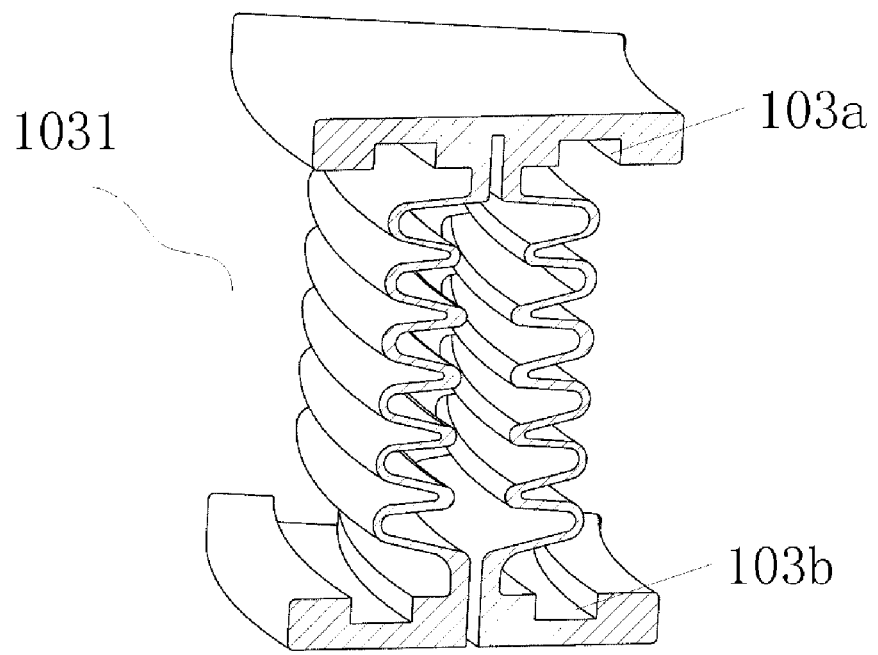

FIGS. 3a-3b illustrate cross-sectional views of a traction sub-structure of a training apparatus in an uninflated state and an inflated state, in accordance with some embodiments of the present disclosure. The plurality of traction sub-structures may be inflatable structures as shown in the figures, i.e., structures that can be expended by inflation and retracted by deflation. For the sake of clarity of description, only one traction sub-structure 1031 is shown in FIGS. 3a and 3b.

As shown in FIGS. 3a and 3b, the retractable traction sub-structure 1031 can be, for example, an inflatable stacked structure 1031. Each stack of the stacked structure 1031 is stacked along a direction from the bottom structure to the top structure. The stacked structure 1031 is configured to be a flat shape in an uninflated state and a stretched shape in an inflated state, and achieve relative movement between the top structure and the bottom structure by inflation and deflation. The stacked structure 1031 can have an internal cavity. In the uninflated state of the internal cavity (as shown in FIG. 3a), the stacked structure 1031 is a flat shape. In the inflated state of the internal cavity (as shown in FIG. 3b), the inflation pressure of the internal cavity is increased, and the stacked structure is bulged, vertically elongated, i.e., axially extended. This will create an axial drive thrust that drives the top bracket and top airbag to push the wearer's neck for axial movement, achieving neck or cervical rehabilitation training. Thus, when the inflatable structure, in particular the inflatable stacked structure 1031, is used as a retractable traction sub-structure, axial traction of the neck can be achieved simply by inflation and deflation. In some embodiments, the length of axial extension of the inflatable stacked structure 1031 can also be controlled by controlling the amount of inflation of the inflatable stacked structure 1031. Optionally, the number of the plurality of traction sub-structures is 7-9. For example, as shown in FIG. 2e, the number may be 8. In some embodiments according to the present disclosure, the upper and lower ends of the internal cavity of the stacked structure 1031 extend to the positions of the upper stuck slot 103a and the lower stuck slot 103b, respectively. Thus, as shown in FIG. 1b, in the inflated state, the internal air pressure of the stacked structure 1031 is increased, and the upper end portion and the lower end portion of the internal cavity are expanded, respectively pressing the upper stuck slot 103a and lower stuck slot 103b on both sides, to make them tightly fitted and firmly snap fitted into the wall of the first stuck slot 104a of the top bracket 104 and the wall of the second stuck slot 105b of the bottom bracket 105, respectively, achieving a close match and preventing loosening. More generally, in addition to the retractable structure by inflation and deflation, the traction sub-structure 1031 can also employ a retractable structure that can be controlled by mechanical principles, such as a spring or a structure similar to a fire elevator.

In some embodiments according to the present disclosure, the stacked structures 1031-1038 may be made of rubber tubes, because the low ductility of the rubber tube may prevent extension elastic deformation to prevent it from becoming uncontrollable, and its good toughness may increase its pressure endurance. Optionally, the stacked structures 1031-1038 may comprise a plurality of rubber tubes stacked and in communication with each other.

In some embodiments according to the present disclosure, as shown in FIGS. 3a and 3b, in the stacked structures 1031-1038, the top rubber tube and the bottom rubber tube respectively have one opening, and the rubber tubes between the top rubber tube and the bottom rubber tube each have both an upper opening and a lower opening, and adjacent rubber tubes communicate through adjacent openings.

In some embodiments according to the present disclosure, a side of each of the top rubber tube and the bottom rubber tube closer to the adjacent rubber tube is provided with two stuck slots 103a, 103b located on both sides of the opening and extending along the opening direction. And a side of the top bracket closer to the rubber tube is provided with a first stuck slot 104a that is matched with the stuck slot 103a of the top rubber tube; and a side of the bottom bracket closer to the rubber tube is provided with a second stuck slot 105b that is matched with the stuck slot 103b of the bottom rubber tube.

In some embodiments of the training apparatus according to the present disclosure, when the traction sub-structures 1031-1038 are inflatable stacked structures, each of the stacked structures 1031 to 1038 and the inflation and deflation device (e.g., an air pump) can be connected through a plurality of air tubes to achieve inflation and deflation of the stacked structure. The air tube may be an air passage that inflates the inflatable stacked structures 1031-1038 and deflates the inflatable stacked structures 1031-1038. Optionally, as shown in FIG. 2c, the outer end portions of the plurality of air tubes may be disposed at the cove 105c of the bottom bracket 105.

Figure 4A:
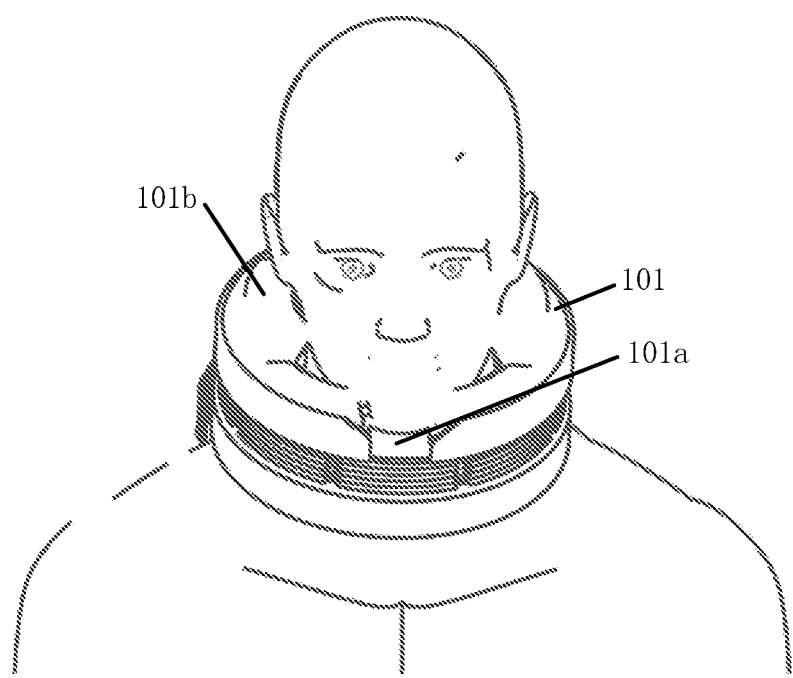
FIGS. 4a-4b schematically illustrate front and side views of a wear effect of a training apparatus in accordance with some embodiments of the present disclosure, respectively.
Figure 4B:
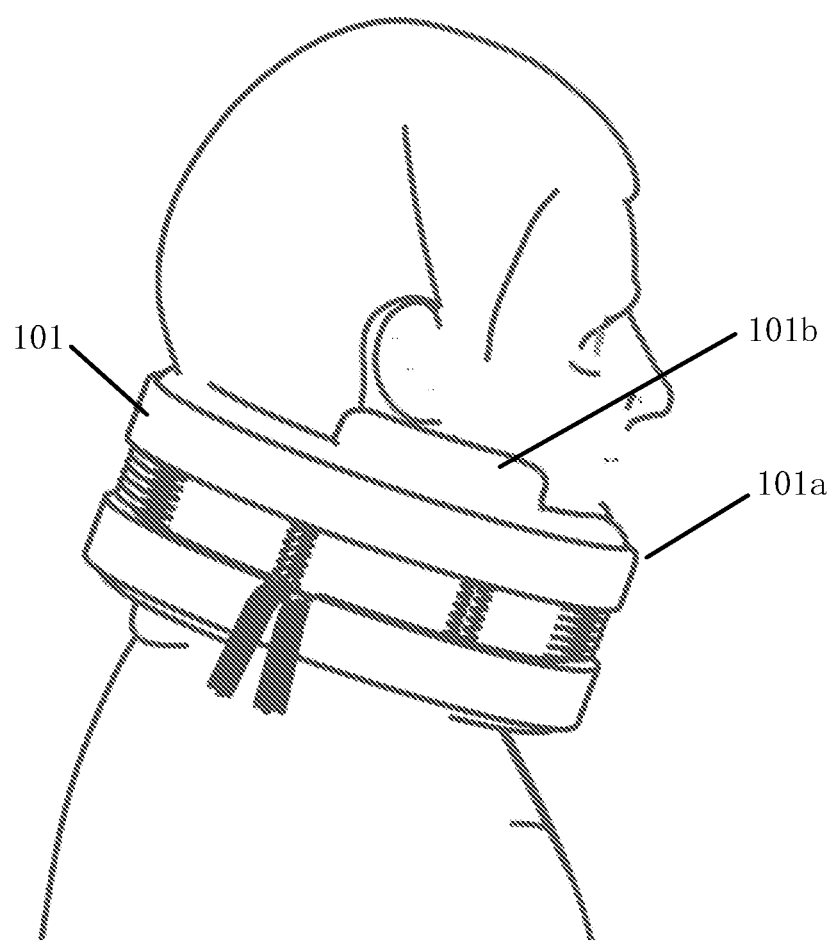

FIGS. 4a-4b schematically illustrate front and side views of a three-dimensional wear effect of a training apparatus in accordance with some embodiments of the present disclosure. As can be seen from the figures, the training apparatus in accordance with some embodiments of the present disclosure, particularly the top bracket and the bottom bracket, may be annular shapes, such that a user's neck may extend therein and the diameter of the training apparatus may be set to be slightly larger than the size of the user's head, which is convenient for the user to wear the training apparatus. As shown in FIGS. 4a-4b, in the inflated state, the notch 101a and the protrusions 101b of the top structure 101 are well fitted to the lower jaw and the neck of the human body, thereby making the wearing comfortable.

Figure 5:
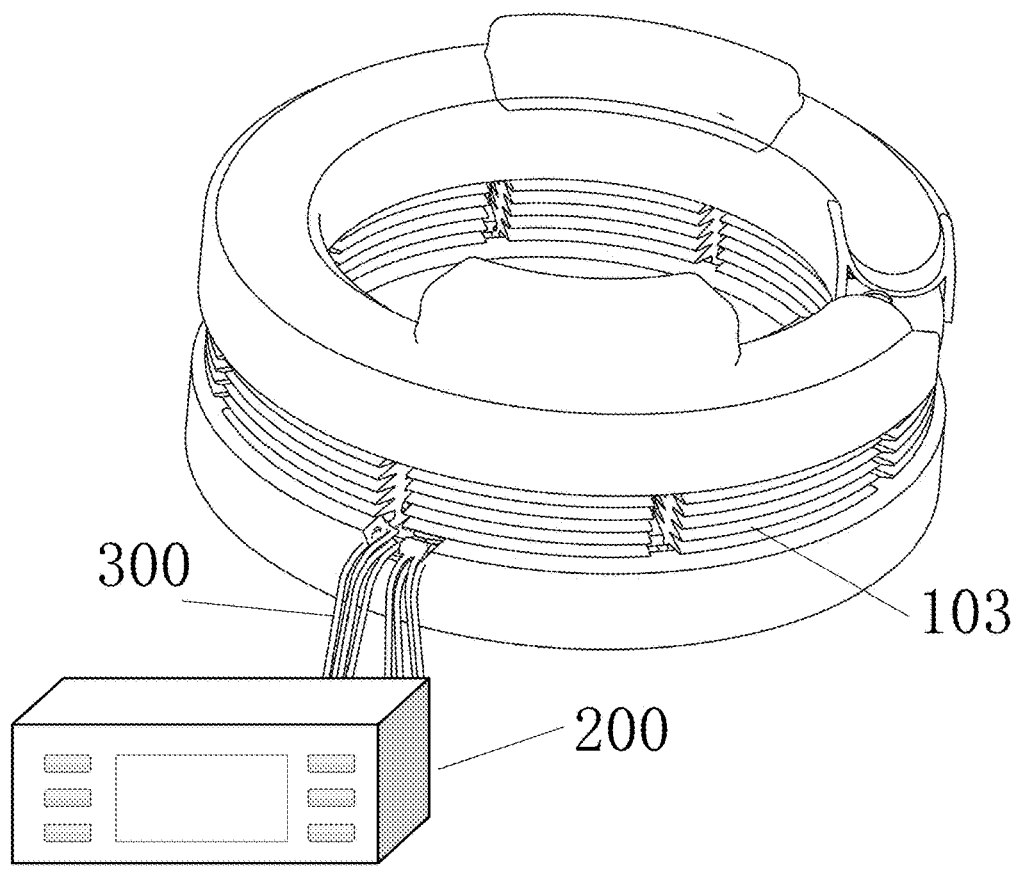
FIG. 5 schematically illustrates a perspective view of a training apparatus in accordance with further embodiments of the present disclosure.

FIG. 5 schematically illustrates a perspective view of a training apparatus in accordance with further embodiments of the present disclosure. Compared with FIG. 1a, the training apparatus shown in FIG. 5 may further comprise a drive device 200 that controls axial extension and retraction of the traction structure 103, which may be detachably connected to the traction structure 103, for example, by a connecting structure 300. This detachable connection allows the traction structure 103 and the drive device 200 to be connected as a whole only when in use, and to be relatively independent individuals when not being used, improving portability.

Figure 6:
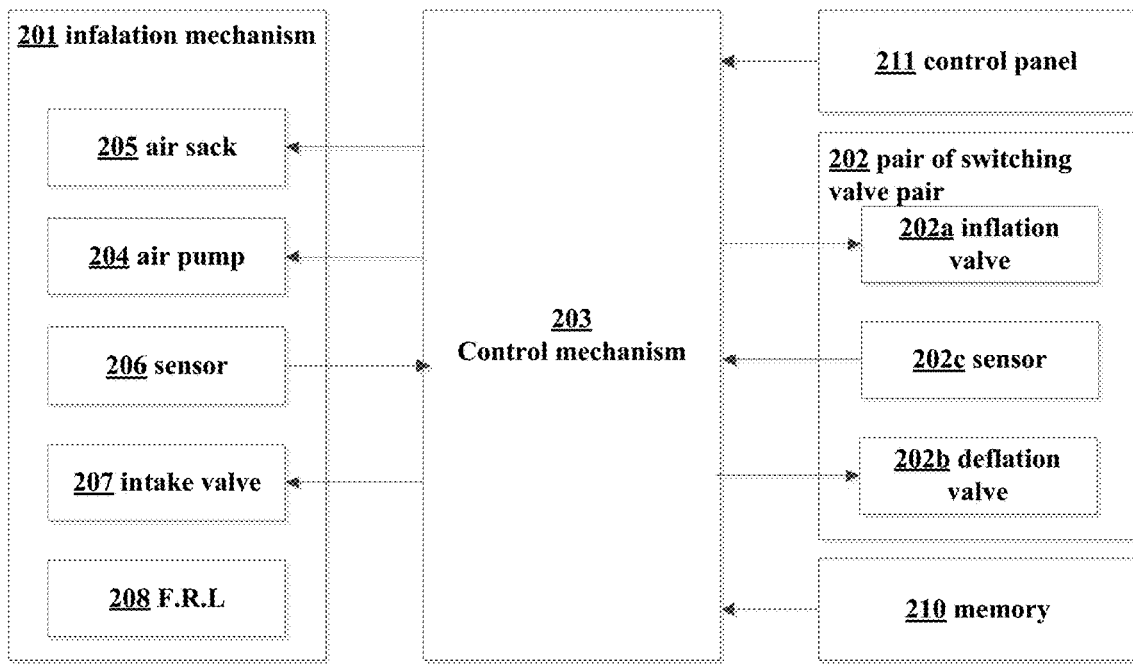
FIG. 6 schematically illustrates a hardware block diagram of a drive device of a training apparatus according to some embodiments of the present disclosure.

FIG. 6 illustrates a hardware block diagram of a drive device of a training apparatus according to some embodiments of the present disclosure, in which arrows indicate flow directions of signals. As shown in FIG. 6, a drive device of a training apparatus according to some embodiments of the present disclosure comprises: an inflation mechanism 201 configured to inflate the stacked structure; a plurality of pairs of switching valves 202 configured to respectively control inflation and deflation of each of the stacked structures; and a control mechanism 203 configured to control the inflation mechanism 201 and the pairs of switching valves 202. Each of the pairs of switching valves 202 can be connected to a corresponding stacked structure by respective air tubes and comprises an inflation valve 202a and a deflation valve 202b for controlling the respective stacked structure to inflate and deflate, respectively.

In some embodiments according to the present disclosure, as shown in FIG. 6, the inflation mechanism 201 may comprise an air pump 204, an air sack 205 configured to be connected to the outlet end of the air pump 204 to store the source gas generated by the air pump 204, a first air pressure sensor 206 for sensing the air pressure in the air sack 205, and an intake valve 207 connected between the outlet end of the air sack 205 and the intake end of the pair of switching valves 202. The intake valve 207 can be automatically controlled by the control mechanism 203 according to a user instruction or can also be manually controlled. In addition, the inflation mechanism 201 may further comprise an F.R.L 208 connected between the intake valve 207 and the pair of switching valves 202 for controlling (reducing) the highest pressure value flowing into the plurality of stacked structures before the source gas reaches the pair of switching valves. In pneumatic technology, the F.R.L is a combination of three source gas treatment components (Filter (F), Regulator (R) and Lubricator (L)), for source gas purification, filtration and pressure reduction, to supply the rated source gas pressure. The Regulator can regulate the source gas to keep the source gas in a constant state, and can reduce the damage to the pair of switching valves 202 and the like due to a sudden change of the source gas pressure. The Filter is used to clean the source gas, and to filter the moisture in the compressed air, to prevent moisture from entering the stacked structure 102 with the gas.

In some embodiments according to the present disclosure, as shown in FIG. 6, the pair of switching valve 202 may further comprise a second air pressure sensor 202c disposed at an outlet end of the inflation valve 202a for sensing an air pressure in the traction structure (e.g., the stacked structure) in real time. The control mechanism 203 can determine whether to turn off the inflation valve 202a or the deflation valve 202b according to the air pressure sensed by the second air pressure sensor 202c, to stop the inflation or deflation process of the inflatable stacked structure. For example, firstly, according to the target traction movement (for example, the front, rear, left, right, up and down traction movement of the neck), the limit degree of the extension or retraction of the stacked structure (for example, the distance of axial extension or retraction) can be determined, and then the internal air pressure measured when the stacked structure is extended and retracted to the limit degree is set to be an inflation threshold and a deflation threshold. After the threshold is determined, the internal air pressure determined in real time at the second air pressure sensor 202c can be compared to the inflation threshold or the deflation threshold during inflation or deflation. The inflation valve 202a or the deflation valve 202b can be turned off when the sensed threshold reaches or exceeds the inflation or deflation threshold, to stop the inflation or deflation. Thus, the turning on and turning off of the inflation valve 202a and the deflation valve 202b can be controlled relatively accurately, thereby accurately controlling the inflation and deflation processes to prevent the air pressure in the stacked structure from being too large or too small.

In some embodiments in accordance with the present disclosure, as shown in FIG. 6, the drive device 200 can further comprise a memory 210 for storing predetermined operational methods or steps for effecting predetermined traction movement for the neck. The control mechanism 203 is configured to control the pairs of switching valves 202 according to stored predetermined operational methods or steps for the neck. Therefore, the user can control the turning on and turning off of each inflation valve and deflation valve in the switching valve group according to the preset operational method, so as to control the inflation and deflation of each traction sub-structure. That is, to drive the top structure to achieve various predetermined traction movement for the neck. For example, as described above, the predetermined traction movement for the neck comprises forward flexion and backwards extension movement of a sagittal plane, left and right flexion movement of a coronal plane, a rotational movement of a horizontal plane, and a tensile traction movement in a vertical direction.

In some embodiments according to the present disclosure, as shown in FIG. 6, the drive device 200 may further comprise a control panel 211 disposed at an outer surface thereof for receiving user instructions. The control mechanism 203 can be configured to control the pairs of switching valves 202 according to user instructions. The control panel 211 can comprise a power switch button for turning the power on, and can also comprise a predetermined traction movement selection interface (such as a corresponding physical button, or touch screen) connected to the control mechanism 203 and the memory 210, for selecting the preset traction movement. Further, the control panel 211 may further comprise respective individual interfaces (such as physical buttons or touch screens) connected to each pair of switching valves, so that the user can freely control the retraction and extension of the respective traction sub-structures according to individual needs, thereby achieving personalized traction movement of the neck.

Figure 7:
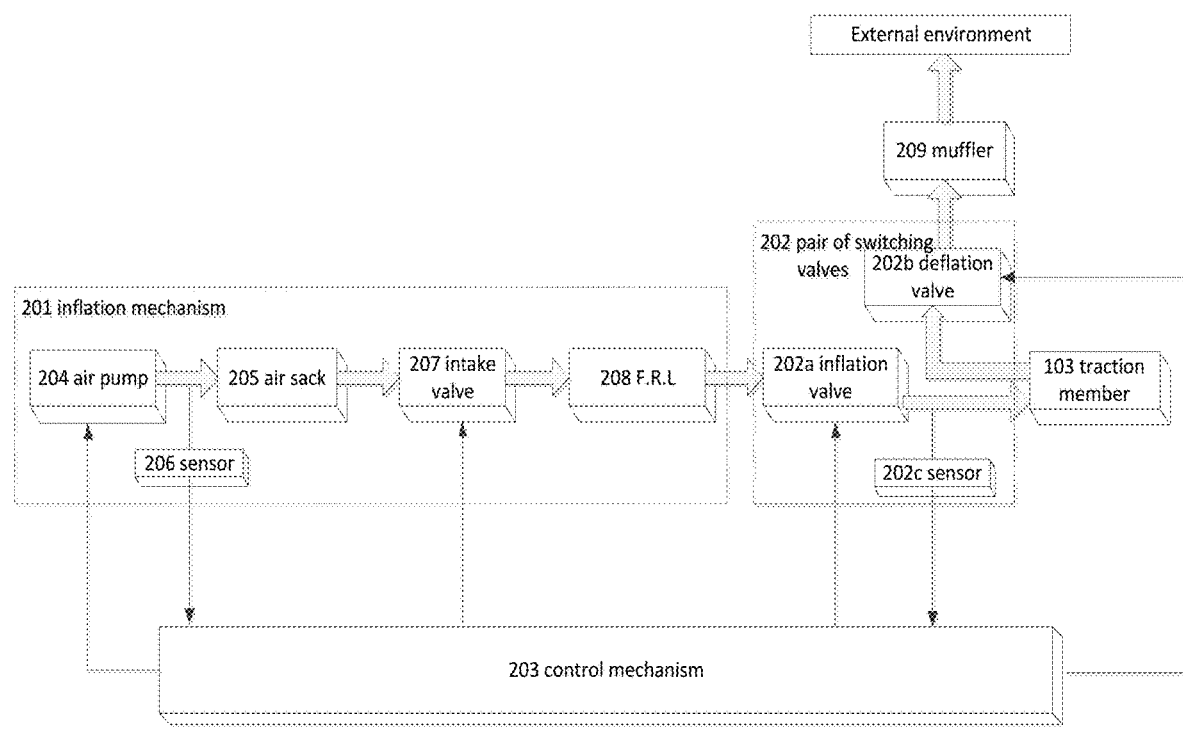
FIG. 7 schematically illustrates a pneumatic circuit and control schematic of a training apparatus in accordance with some embodiments of the present disclosure.

FIG. 7 illustrates a pneumatic circuit and control schematic of a training apparatus in accordance with some embodiments of the present disclosure, in which thick arrows indicate airflow directions and thin solid arrows indicate flow directions of signals. As shown in FIG. 7, in the training apparatus according to the present disclosure, the drive device inflates and deflates the traction structure 103 by controlling the inflation mechanism 201 and the pair of switching valves 202 by the control mechanism 203. The specific operation process of the drive device is as follows: when the air pump 204 is controlled to be turned on, for example, by the central controller 203, the gas from the air pump 204 first enters the air sack 205 and then reaches the intake valve 207 (which can be regarded as the main switch of the pneumatic circuit system and can control the subsequent inflow of the source gas). When the intake valve 207 is controlled to be turned on, for example, by the control mechanism 203, the gas flows to the F.R.L 208. The F.R.L 208 performs depressurization process to the inflowing source gas, to control the highest value of the air pressure flowing into the subsequent circuit. After the depressurization treatment, the gas reaches the group of the pairs of switching valves, i.e., the plurality of pairs of switching valves 202 (comprising the inflation valve 202a and the deflation valve 202b) corresponding to the respective traction sub-structures of the traction structure 103, respectively. At this time, the respective ones of pairs of switching valves cooperate with each other to control the inflation and deflation of their corresponding traction sub-structure s, thereby achieving corresponding traction movement. Further, in the above process, the first and second air pressure sensors 206, 202c can also sense the air pressure in the air sack 205 and the traction structure 103, respectively, and transmit the sensed results to the control mechanism 203 in real time. The control mechanism 203 can control the turning on and turning off of the air pump 204 and/or the pairs of switching valves 202 accordingly based on the pressure sensed by the first and/or second air pressure sensors 206, 202c.

In some embodiments according to the present disclosure, the drive device may further comprise a muffler 209 disposed at an outlet end of the deflation valve 202b, to reduce exhaust noise when the deflation valve 202b is turned on to deflate the traction structure 103.

Figure 8:
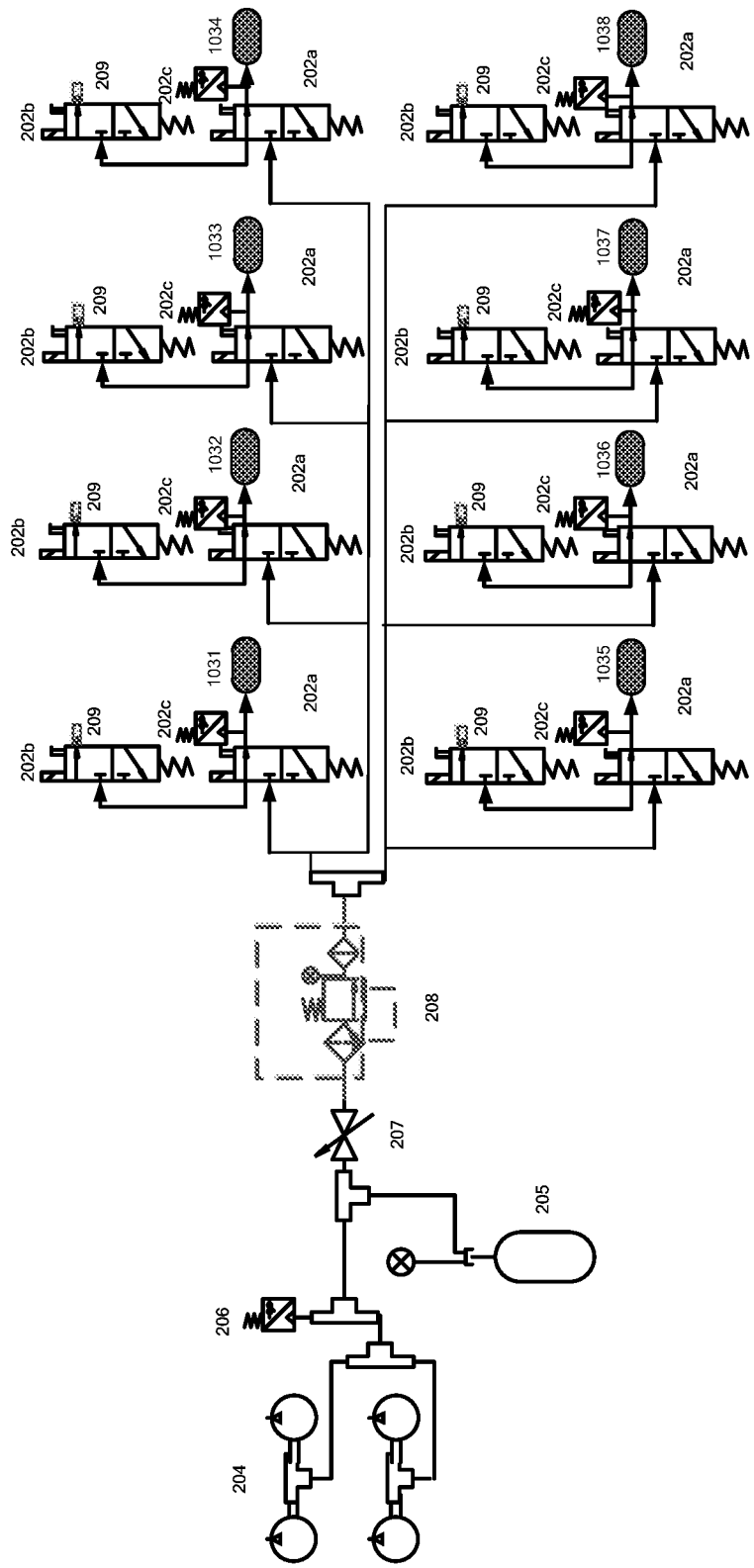
FIG. 8 schematically illustrates a physical connection diagram of various components of a training apparatus in accordance with some embodiments of the present disclosure.

FIG. 8 illustrates a physical connection diagram of various components of a training apparatus in accordance with some embodiments of the present disclosure. As shown in FIG. 8, the air pump 204 comprises one or more micropumps. According to the flow rate of the gas generated by the micropump 204, one can determine how many micropumps are needed simultaneously to supply gas to ensure sufficient source gas generation. One or more (two shown in the figure) micropumps 204 may be connected to the air sack 205 via the air tube and a tee. Further, the air pump 204 can be an electric pump or a manual pump.

As shown in FIG. 8, the first air pressure sensor 206 can be connected between the micro air pump 204 and the air sack 205 through the tee, to sense the internal pressure value of the air sack 205 in real time. At the same time, a pressure gauge can be introduced at the end portion of the air sack, to visually present the pressure value of the source gas inside the air sack 205 to the user. The first air pressure sensor 206 can transmit the sensed data to the control mechanism in real time, such that the control mechanism can control the turning on and turning off of the air pump 204 based on the pressure value inside the air sack 205 sensed by the first air pressure sensor 206. Exemplarily, when the sensed pressure value is greater than the upper limit of the pressure value set in the controller, the control mechanism may issue a stop instruction to control the micropump to stop working; and when the pressure value is less than the lower limit of the pressure value set in the controller, the control mechanism can issue a turning on instruction to control the micropump to start working. The introduction of the first air pressure sensor 206 makes it possible to control the pressure of the source gas inside the air sack 205 within a relatively reasonable range (between the upper limit and the lower limit) to avoid problems caused by too large or too small pressure values. For example, too large pressure inside the air sack 205 may cause damage due to unbearability; and if the pressure is too small, the stacked structure may not be fully driven to extend.

In a training apparatus according to some embodiments of the present disclosure, the pair of switching valves 202 may employ a solenoid valve group. Because the solenoid valve is more sensitive and has a shorter response time (for example, as short as several milliseconds) compared to other types of valves, it is a relatively high-speed switching valve, which allows the gas pressure in the stacked structure to be quickly adjusted to achieve flexible and versatile control of the neck traction movement and makes it easy to implement more complex traction movement, such as rotational movement on a horizontal plane. In addition, the solenoid valve is simple in structure, small in size, and low in power consumption, and thus is well suited for use in a portable training apparatus according to the present disclosure. Of course, the pair of switching valves 202 can also be an electric valve group or other drive types of valve groups, as long as it is suitable for sensitive (high-speed) control and portability requirements.

The inflation valve 202a and the deflation valve 202b in the pair of switching valves 202 can be connected to the air passage through a tee, wherein the intake end of the inflation valve 202a is connected to the inflation mechanism 201 (i.e., the F.R.L 208 therein), and the outlet end is connected to the tee. The inlet end of the deflation valve 202b is connected to the tee, and the outlet end is connected to the external environment, that is, serving as the outlet of the corresponding stacked structures 1031-1038. It should be noted that, for the sake of clarity, only one pair of switching valves, namely a set of inflation valve and deflation valve, is shown in FIGS. 6 and 7. And in fact, as shown in FIG. 8, each traction sub-structure or stacked structure 1031-1038 can correspond to one pair of switching valves, i.e., one inflation valve and one deflation valve. Thus the total number of switching valves is twice that of the stacked structures 1031-1038. For example, FIG. 8 shows eight stacked structures, so that the corresponding pairs of switching valves has a total of eight pairs of switching valves, and a total of 16 single-switching valves, eight of which are inflation valves and eight of which are deflation valves. The control mechanism respectively controls the pairs of switching valves in the switching valve group to work in cooperation with each other to achieve inflation or deflation (i.e., pressurization or depressurization) of the corresponding stacked structure to form axial extension and retraction, thereby driving the top airbag movement and achieving multi-degree-of-freedom traction movement of the neck.

In some embodiments according to the present disclosure, as shown in FIG. 8, the muffler 209 is disposed at the outlet end of the deflation valve 202b, to reduce exhaust noise when the deflation valve 202b is turned on to deflate the stacked structures 1031-1038.

Figure 9:
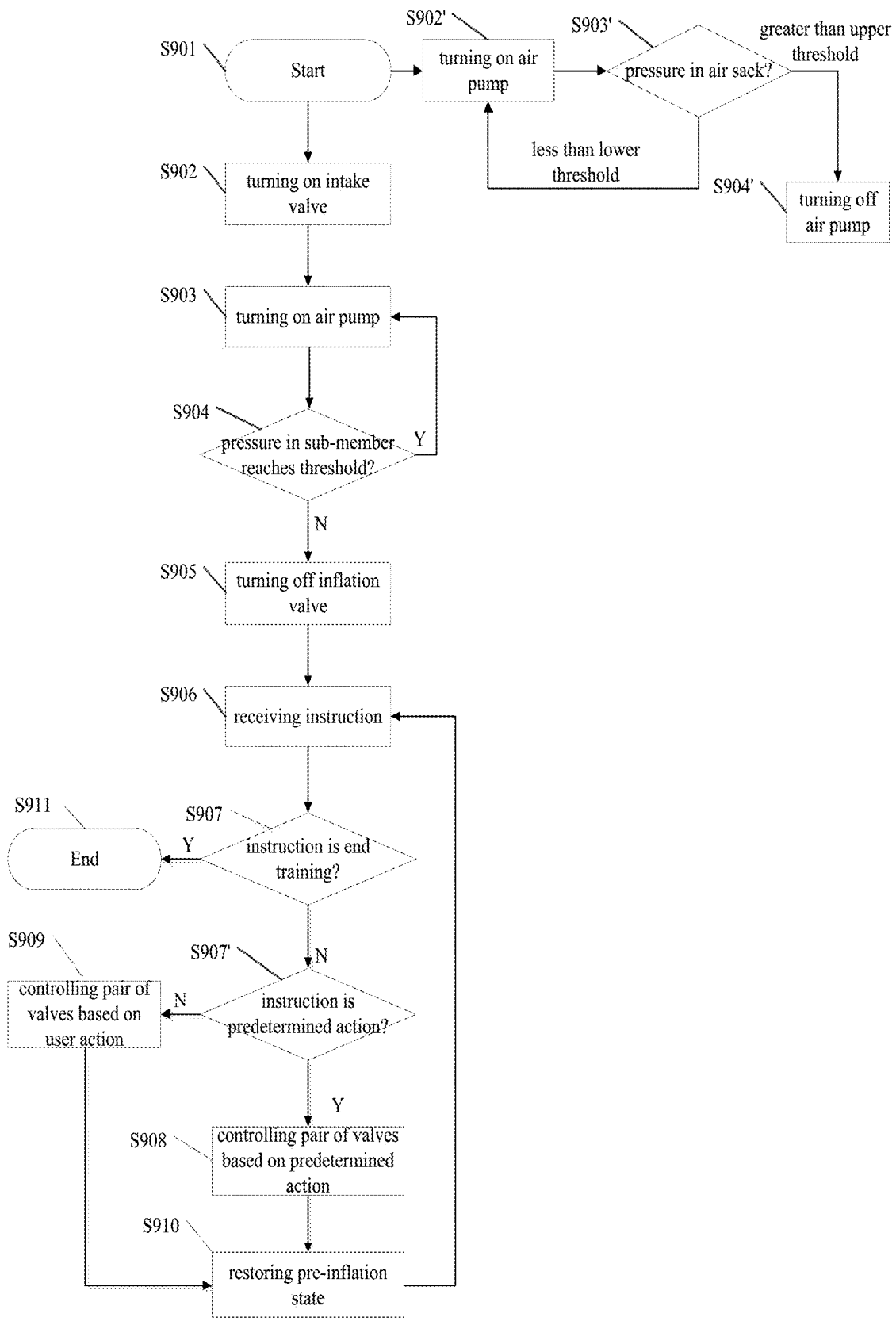
FIG. 9 schematically illustrates an operational flowchart of a training apparatus in accordance with some embodiments of the present disclosure.

FIG. 9 illustrates a workflow diagram of a training apparatus in accordance with some embodiments of the present disclosure. Hereinafter, for the purpose of explanation, eight traction sub-structures are taken as an example, and the positions of which on the main structure are respectively corresponding to the positions of the following eight muscle tissues around the neck of the human body: the erector spinae at the direct rear side, the left trapezius at the left rear side, the left sternocleidomastoid at the left side, the left platysma at the left front side, the sternohyoid muscle at the direct front side, the right platysma at the right front side, the right sternocleidomastoid at the right side, and the right trapezius at the right rear side.

In general, the workflow of a training apparatus in accordance with some embodiments of the present disclosure comprises the following steps. First, the eight traction sub-structures are pre-inflated such that the extension of the traction sub-structures drives the top airbag to support the wearer's head, keeping the wearer's neck in an upright state. Then, the multi-degree-of-freedom traction movement is achieved by controlling the inflation and deflation of the respective traction sub-structures, such as forward flexion and backwards extension movements in a sagittal plane, left and right flexion movements in a coronal plane, a rotational movement in a horizontal plane, and a tensile traction movement in a vertical direction.

In one example, after the user wears the training apparatus, as shown in the flow chart of FIG. 9, in step S901, the user can turn on the training apparatus by triggering, for example, a power switch on the control panel.

Next, in step S902, the control mechanism turns on the intake valve of the inflation mechanism. At the same time, in step S902', the control mechanism turns on the air pump; then, the control mechanism controls the turning on and turning off of the air pump according to the pressure value in the air sack sensed by the first air pressure sensor in real time. Specifically, in step S903', the control mechanism compares the pressure value sensed in real time with a preset threshold: if the sensed pressure value is greater than the preset upper threshold, the air pump is turned off in step S904'; When the sensed pressure value is less than the preset lower threshold, the turning on of the air pump is kept, thereby controlling the pressure in the air sack to be in a reasonable range. The upper threshold and the lower threshold can be preset as needed.

After step S902, the operational flow enters the pre-inflation phase. Specifically, at step S903, the control mechanism controls the pairs of switching valves to turn on all of the inflation valves, to inflate and pressurize the traction sub-structures. During the inflation process, at step S904, the second air pressure sensor senses in real time whether the gas pressure in the traction sub-structure reaches a preset pre-inflation pressure threshold: if so, the inflation valve is turned off at step S905, and the pre-inflation phase ends; otherwise the inflation valve is continued to be kept on for inflation until the preset value is reached. Here, the above-mentioned air pressure preset value for defining whether the pre-inflation process is completed may be set by: firstly, pre-inflating the traction sub-structure until the traction structure is extended such that the top structure just touches the wearer's head and the wearer's neck is kept in an upright state, and then the gas pressure value inside the traction structure at this time is measured, and the pressure value can be used as the above-mentioned pre-inflation pressure threshold.

After the pre-inflation is completed, in step S906, the control mechanism can receive an input instruction from the user. For example, the user can input a specific control instruction through a control panel or a touch screen on the drive device. The instructions may comprise, for example, selecting a predetermined neck traction movement mode stored in the memory via a selection interface on the control panel or the touch screen, or setting the specified specific traction movement via e.g. a separate interface (such as the physical button or touch button) corresponding to each pair of the switching valves on the panel by the user to form personalized traction movement on the neck. Additionally, the control instruction can also comprise an instruction to turn off the training apparatus, such as by a power switch.

Subsequently, in steps S907 and S907', the control mechanism determines regarding to the received user input instructions to perform different movement according to different instructions. First, in step S907, it is determined whether the instruction is to end the neck training, i.e., turn off the training apparatus (or turn off the power), and if so, the workflow proceeds to the end step S911; if not, the workflow proceeds to the next decision step S907'. In step S907', if the received instruction is the predetermined traction mode selected by the user, the workflow proceeds to step S908, and the control mechanism controls the turning on and turning off of the pairs of switching valves based on the specific process of the predetermined traction movement stored in the memory; if the instruction is the personalized traction movement input by the user, the workflow proceeds to step S909, and the control mechanism controls the turning on and turning off of the pairs of switching valves based on the specific movement of the respective traction sub-structures input by the user. In the end step S911, the control mechanism can control the pairs of switching valves to completely deflate the respective traction sub-structures, and then the power switch, the total intake valve and the pairs of switching valves are turned off.

After the above-mentioned traction movement step S908 or S909 is completed, the workflow proceeds to step S910, and the control mechanism may control the traction sub-structures to restore or maintain the pre-inflation state, and to wait for the next operation instruction, that is, proceeding to step S906. Subsequently, the control mechanism determines whether to re-execute the traction movement (S908 or S909) or completely end the neck training (S911) according to the instruction input by the user again.

Hereinafter, the first traction sub-structure corresponding to the erector spine and the corresponding pair of solenoid valves are taken as an example to describe how the pair of switching valves can inflate and deflate the traction sub-structure. The pair of switching valves corresponding to the first traction sub-structure comprises an inflation valve and a deflation valve, which are combined to cause the first traction sub-structure to be in one of three states: inflation, holding, and deflation. Specifically, when the inflation valve is turned on and the deflation valve is turned off, the source gas enters the first traction sub-structure through the inflation valve, and the first traction sub-structure is in an inflated and pressurized state, causing it to extend to generate an axial pushing force, thereby pulling up the corresponding part of the neck upwards. When the inflation valve is turned off and the deflation valve is turned off, the external source gas cannot enter and the internal gas cannot flow out, and the air pressure inside the first traction sub-structure remains the original state, and there is no influence on the neck at this time. When the inflation valve is turned off and the deflation valve is turned on, the internal gas enters the external environment through the deflation valve, and the first traction sub-structure is in a deflated and depressurized state, causing it to extend to generate an axial retractive force, thereby pulling down the corresponding part of the neck downwards. Obviously, the inflation valve and the deflation valve cannot be turned on at the same time, because in this way the external source gas entering from the inflation valve will directly flow to the external environment via the deflation valve, there is no influence on the internal pressure of the first traction sub-structure, and the source gas generated by the inflation mechanism (i.e., the air pump) is wasted, which is not worth it.

The above describes how to achieve axial movement by controlling the extension and retraction of a single traction sub-structure by inflation and deflation using the switching valve. Next, based on the working principle of the traction structure of the training apparatus according to the present disclosure described above with reference to FIG. 2e, how the plurality of inflatable traction sub-structures cooperate with each other by inflation and/or deflation operations to complete the multi-degree-of-freedom traction movement of the neck is described. For the sake of clarity, the plurality of traction sub-structures are first to eighth inflatable stacked structures respectively corresponding to the erector spinae at the direct rear side, the left trapezius at the left rear side, the left sternocleidomastoid at the left side, the left platysma at the left front side, the sternohyoid muscle at the direct front side, the right platysma at the right front side, the right sternocleidomastoid at the right side, and the right trapezius at the right rear side, where both the top and bottom structures are airbags.

For example, a training apparatus according to the present disclosure can achieve a 4-degree-of-freedom traction movement as follows:

The forward flexion/backwards extension movement in a sagittal plane in a first degree of freedom: inflating and pressurizing the first stacked structure to cause axial extension movement, while deflating and depressuring the fifth stacked structure to cause axial retraction movement, to push the top bracket and the top airbag to perform forward flexion movement of a sagittal plane to drive the wearer's neck to complete the forward flexion movement of a sagittal plane. Instead, inflating and pressurizing the fifth stacked structure to cause axial extension movement, while deflating and depressuring the first stacked structure to cause axial retraction movement, thereby driving the wearer's neck to complete the backwards extension movement in a sagittal plane.

The right/left flexion movement in a coronal plane in a second degree of freedom: inflating and pressurizing the third stacked structure to cause axial extension movement, while deflating and depressuring the seventh stacked structure to cause axial retraction movement, thereby driving the wearer's neck to complete the right flexion movement of a coronal plane. Instead, inflating and pressurizing the seventh stacked structure to cause axial extension movement, while deflating and depressuring the third stacked structure to cause axial retraction movement, thereby driving the wearer's neck to complete the left flexion movement in a coronal plane.

The rotational movement in a horizontal plane in a third degree of freedom: inflating and pressurizing the first to eighth stacked structures sequentially in a clockwise manner so that they are sequentially extended in the axial direction, while deflating and depressuring the stacked structures opposite to the stacked structures that are being inflated and pressurized, so that they are sequentially retracted in the axial direction, thereby driving the wearer's neck to complete the clockwise rotational movement of the horizontal plane. Instead, inflating and pressurizing the first to eighth stacked structures sequentially in a counterclockwise manner so that they are sequentially extended in the axial direction, while deflating and depressuring the stacked structures opposite to the stacked structures that are being inflated and pressurized, so that they are sequentially retracted in the axial direction, thereby driving the wearer's neck to complete the counterclockwise rotational movement in the horizontal plane.

The tensile traction movement in a vertical direction in a fourth degree of freedom: at the same time, the eight stacked structures are inflated and pressurized so that they are simultaneously extended in the vertical axial direction, which can drive the wearer's neck to complete the tensile traction movement in a vertical direction.

It should be noted that the "control mechanism" described herein may employ a general control mechanism (chip), a single chip microcomputer, etc., capable of transmitting and receiving signals, operating and processing information and data, and automatically running, and may comprise drive circuits or other types of drive devices for directly driving the respective components (e.g., inflation mechanisms and switching valve groups, etc.) depending on the drive method, such as electric, hydraulic, pneumatic, electromagnetic, etc. For the sake of clarity and simplification, these drive devices or drive circuits are omitted herein and what is directly stated herein is that the control mechanism controls the various components in the drive device, such as the inflation mechanism and the switching valve group. In addition, the drive device may also comprise a power source (fixed power source (mains power) or mobile power source (battery)) for supplying power to each component and the driving circuit, and if necessary, the power source can supply power to the drive circuit and control mechanism after passing through the buck regulator circuit (transformer).

Furthermore, "detachable connection" as used herein refers to the joining of two structures together by means of a detachable and/or removable connection such as bonding, snap-fitting, riveting, threading, over-fitting, and the like, and the connection between the A structure and the B structure can be removed by, for example, heating, pulling, pressing, impacting, vibrating, etc., without damaging and/ or breaking the A structure and B structure, so as to facilitate the replacement and recycling of components.

It should be noted that, in the claims, the term "comprising" and the variants thereof does not exclude the presence of other elements or steps that are not stated in the claims; The article "a" or "an" does not exclude a plurality.

While particular embodiments of the present disclosure have been shown and described, it will be apparent to those skilled in the art that, a number of changes and modifications can be made in its broader aspects without departing from the disclosure. Therefore, the appended claims shall comprise all such changes and modifications within their scopes, as falling within the true spirit and scope of this disclosure.

The invention claimed is:

1. A training apparatus comprising:
a top structure;
a bottom structure;
and a traction structure disposed between the top structure and the bottom structure, wherein the traction structure is configured to be retractable along an axial direction of the top structure or the bottom structure to achieve relative movement between the top structure and the bottom structure;
the traction structure further comprises:
a plurality of traction sub-structures, each of the plurality of traction sub-structures configured to be independently retractable along the axial direction and each traction sub-structure comprising an inflatable stacked structure, each of the inflatable stacked structures is stacked along a direction extending from the bottom structure to the top structure,
and the inflatable stacked structure is configured to be a flat shape in an uninflated state and a stretched shape in an inflated state to achieve the relative movement between the top structure and the bottom structure by inflation and deflation;
wherein each of the inflatable stacked structures further comprises:
a top rubber tube, a bottom rubber tube, and a plurality of rubber tubes between the top rubber tube and the bottom rubber tube, wherein the top rubber tube and the bottom rubber tube each respectively have one opening, and the plurality of rubber tubes between the top rubber tube and the bottom rubber tube each have an upper opening and a lower opening, and adjacent rubber tubes communicate through adjacent openings;
the training apparatus further comprising:
a top bracket disposed between the top structure and the traction structure, a bottom bracket disposed between the bottom structure and the traction structure, wherein each of the top bracket and the bottom bracket comprise an annular structure, and the plurality of traction sub-structures are disposed on the bottom bracket to be connected to the top bracket, and the plurality of traction sub-structures are sequentially spaced along the annular structure;
wherein each of the top rubber tube and the bottom rubber tube is provided with two stuck slots located on either side of the opening and extending along a direction of the opening;
a side of the top bracket closer to the top rubber tube is provided with a first stuck slot that is matched with the two stuck slots of the top rubber tube:
a side of the bottom bracket closer to the bottom rubber tube is provided with a second stuck slot that is matched with the two stuck slots of the bottom rubber tube;

a side of the top bracket away from the top rubber tube is provided with a first groove configured to receive the top structure;

and a side of the bottom bracket away from the bottom rubber tube is provided with a second groove configured to receive the bottom structure.

2. The training apparatus according to claim 1, wherein the top structure and the bottom structure comprise annular airbags.

3. The training apparatus of claim 1, further comprising a drive device configured to control extension and retraction of the plurality of traction sub-structures, and wherein the drive device comprises: an inflation mechanism configured to inflate each of the inflatable stacked structures; a plurality of pairs of switching valves configured to respectively control inflation and deflation of each of the inflatable stacked structures, each pair of switching valves comprising an inflation valve and a deflation valve; and a control mechanism configured to control the inflation mechanism and the plurality of pairs of switching valves.

4. The training apparatus according to claim 1, wherein the inflation mechanism comprises: one or more air pumps configured to generate a source gas; an air sack configured to be connected to the one or more air pumps to store the source gas; an intake valve connected to an outlet end of the air sack, and wherein the control mechanism is configured to control turning on and turning off of the intake valve.

5. The training apparatus according to claim 4, wherein the inflation mechanism further comprises: a first air pressure sensor connected between the one or more air pumps and the air sack, the first air pressure sensor being configured to sense an internal pressure of the air sack, wherein the control mechanism is configured to: compare the pressure sensed by the first air pressure sensor with a preset upper threshold and a preset lower threshold, and turn off the one or more air pumps in response to the sensed pressure being greater than the preset upper threshold, and turn on the one or more air pumps in response to the sensed pressure being less than the preset lower threshold.

6. The training apparatus according to claim 5, wherein each of the plurality of pairs of switching valves further comprises: a second air pressure sensor disposed at an outlet end of the inflation valve, the second air pressure sensor being configured to sense an air pressure in each of the inflatable stacked structures, wherein the control mechanism is configured to turn on and turn off the inflation valve and/or the deflation valve according to the air pressure sensed by the second air pressure sensor.

7. The training apparatus according to claim 6, wherein the inflation mechanism further comprises: a filter, a regulator, and a lubricator (F.R.L), connected between the intake valve and the pair of switching valves.

8. The training apparatus according to claim 5, wherein each of the plurality of pairs of switching valves further comprises:

a second air pressure sensor disposed at an outlet end of the inflation valve, the second air pressure sensor being configured to sense an air pressure in the stacked structure, wherein the control mechanism is configured to turn on and turn off the inflation valve and/or the deflation valve according to the air pressure sensed by the second air pressure sensor.

9. The training apparatus according to claim 7, wherein the inflation mechanism further comprises:

an F.R.L connected between the intake valve and the pair of switching valves.

10. The training apparatus according to claim 4, wherein the drive device further comprises a memory configured to store operational steps of a predetermined traction movement, and wherein the control mechanism is configured to control the plurality of pairs of switching valves according to the operational steps of the predetermined traction movement stored in the memory.

11. The training apparatus according to claim 4, wherein each deflation valve of the plurality of pairs of switching valves comprises a muffler disposed at an outlet end of the deflation valve.

12. The training apparatus according to claim 10, wherein the predetermined traction movement comprises forward flexion and backwards extension movement in a sagittal plane, left and right flexion movement in a coronal plane, a rotational movement in a horizontal plane, and a tensile traction movement in a vertical direction.

\* \* \* \* \*